(12) United States Patent
Stein et al.

(10) Patent No.: US 6,582,690 B1
(45) Date of Patent: Jun. 24, 2003

(54) PROCESS FOR TREATING TUMORS WITH CYTOTOXIC SUBSTANCES

(75) Inventors: Ulrike Stein, Berlin (DE); Wolfgang Walther, Berlin (DE); Peter Schlag, Berlin (DE)

(73) Assignee: Max-Delbrück-Centrum für Molekulare Medizin, Berlin (DE)

( * ) Notice: Subject to any disclaimer, the term of this patent is extended or adjusted under 35 U.S.C. 154(b) by 0 days.

(21) Appl. No.: 09/273,066

(22) Filed: Mar. 19, 1999

Related U.S. Application Data

(63) Continuation of application No. PCT/EP97/05133, filed on Sep. 19, 1997.

(30) Foreign Application Priority Data

Sep. 20, 1996 (EP) .............................................. 96250206

(51) Int. Cl.$^7$ ................................................ A61K 38/21
(52) U.S. Cl. .................... 424/85.4; 424/85.1; 424/85.2; 514/2; 514/34
(58) Field of Search ............................ 424/85.4, 85.1, 424/85.2; 514/2, 34

(56) References Cited

U.S. PATENT DOCUMENTS 5,817,321 A * 10/1998 Alakhov et al.
5,855,866 A * 1/1999 Thorpe et al.
5,916,871 A * 6/1999 Johnson

FOREIGN PATENT DOCUMENTS

WO    PCT/US95/08085    7/1994

OTHER PUBLICATIONS

U. Stein et al., Modulation of Mdr1 expressing by cytokines, etc., Brit. Jnl. of Cancer, (1996), 74, 1384–1391.
U. Stein et al., Reversal of Multidrug Resistance, etc., J. Nat. Canc. Inst., (1996), 88, 1383–1391.
W. Walther et al., Employment of the mdr1 promoter, etc., Gene Therapy, (1997), 4, 544–552.
W. Walther et al., Gene Transfer of Human TNF into glioblastoma etc., Int. J. Cancer, (1995), 41, 832–839.
W. Walther et all., Influence of cytokines on mdr1 expression, etc., Cancer Res. Clin. Oncol (1994), 120, 471–478.
U. Regenass, et al., TNF in combination with cytostatic agents, CibaOGeigy (1986).
R. Nabioullin et al., Influence of systemic chemotherapy on anti–P–glycoprotein, etc., Jpn. J. Clin. Oncol., (1995), 25, 124–130.
R. L. X. Ho, et al., Development of safe and effective adriamycin, etc., Oncology Resch., (1993), 5, 373–381.

* cited by examiner

*Primary Examiner*—Leon B. Lankford, Jr.
(74) *Attorney, Agent, or Firm*—Goodwin Procter LLP

(57) ABSTRACT

The invention concerns a cytotoxic, MDR-associated substance for producing a therapeutic agent for tumor therapy, which is characterized by a) the tumor cells of a tumor patient are chemosensitized with a cytokine, b) the scope of expression of one or more MDR-associate genes (e.g. mdrl, Mrp, Lrp) in the tumor tissues of the patient is determined according to the beginning of the cytokine treatment, c) the time domain is determined, in which the expression of one or more MDR-associate genes is substantially reduced by the cytokine treatment, d) the patient is treated in the determined time domain ("therapeutic window") with a therapeutically effective amount of a cytotoxic, MDR-associated substance, the effectiveness of which is influenced (enhanced) by the expression of one or more MDR-associate genes. The use of said substance leads to an improved tumor therapy.

5 Claims, No Drawings

PROCESS FOR TREATING TUMORS WITH CYTOTOXIC SUBSTANCES

This is a continuation of international application PCT/EP97/05133, filed on Sep. 19, 1997.

FIELD OF THE INVENTION

The present invention relates to a process for tumor treatment with cytokines, the monitoring of multidrug resistance (MDR)-associated genes and subsequent treatment with cytotoxic substances, as well as the use of these substances for producing a drug.

BACKGROUND

Efficiency of chemotherapy of malignant diseases is often limited by the simultaneous resistance towards structurally and functionally unrelated cytotoxic compounds. This multidrug resistance (MDR) phenomenon is mediated by MDR-associated genes such as mdr1, MRP (MDR-associated protein) and/or LRP (lung resistance protein). The classical resistance type of MDR is caused by overexpression of the mdr1 gene product, the P-glycoprotein (Pgp) (U. A. German et al., Sem. Cell. Biol. 4, (1993):63–76). In normal tissues Pgp expression has been detected mainly in epithelial cells with excretory or secretory function (A. T. Fojo et al., Proc. Natl. Acad. Sci. USA,84 (1987):265–269). In tumors of almost every localization, including in brain tumors, expression of the mdr1 gene has been observed (K. Nooter et al., Br. J. Cancer 63 (1991):663–669 and M. Mousseau et al., Eur. J. Cancer (1993):753–759). There exist a number of different approaches for the so-called reversal or overcoming of MDR that are mainly based on the inhibition of Pgp as drug-efflux-pump, but that also imply toxic side effects (J. Kellen, Anticancer Res. 13 (1993):959–961). Calcium channel blockers, alkaloids, Pgp-specific antibodies etc. are among these resistance modifying agents.

W. Walther and U. Stein describe in J. Cancer Research and Clinical Oncology (W. Walther et al., J: Cancer Res. Clin. Oncol. 120 (1994):471–478) and in British Journal of Cancer (U. Stein et al., Br. J. Cancer.47 (1996):1384–1391) the influence of cytokines on mdr1 expression in human colon carcinoma cell lines. It has been found, that 48 hours and 72 hours detectable reduction in mdr1 expression can be seen after cytokine treatment. The cell lines LoVo, SW480, LS174T, HCT15 and HCT116 were used for these experiments. TNFα, IFNy and IL-2 were utilized as cytokines. Vincristine and doxorubicin were used as cytostatic substances. The cytokine-mediated effects on mdr1 gene expression, associated with chemosensitization, have also been shown for the gene transfer of TNFα into human U373 MG glioblastoma cells (W. Walther et al. Int. J. Cancer (1995):832-hours and 72 hours after cytokine treatment detectable reduction in mdr1 expression can be seen. The cell lines LoVo, SW480, LS174T, HCT15 and HCT116 were used for these experiments. TNFα, IFNy, and IL-2 were utilized as cytokines. Vincristine and doxorubicin were used as cytostatic substances. The cytokine-mediated effects on mdr1 gene expression, associated with chemosensitization, have also been shown for the gene transfer of TNFα into human U373 MG glioblastoma cells (W. Walther et al. Int. J. Cancer (1995):832–8 839). It has been pointed out in agreement with other authors (e.g. C. H. Evans et al. Cancer Res. 52 (1992):5893–5899 and K. E. Sampson et al. Cancer Lett. 68 (1993):7–14), that modulation of mdr1/Pgp expression is an interesting alternative to conventional therapies for MDR reversal. A suitable procedure for this is neither proposed nor suggested.

DESCRIPTION OF THE INVENTION

It is an object of the present invention to provide a process for modulation of mdr1/Pgp expression. Using this process tumors can be treated, which until now were not or only minimally susceptible such a therapy with certain MDR-associated cytotoxic substances in chemotherapy. Thus, colorectal carcinomas would, in contrast to previous therapies with antimetabolites, be better susceptible therapies with MDR-associated cytostatics such as vinca alkaloids and/or anthracyclines.

The invention utilizes a cytotoxic, MDR-associated substance for the generation of a therapeutic for tumor therapy by chemosensitization of tumor cells of a cancer patient with a cytokine, the determination of the level of one or several MDR-associated genes (e.g. mdr1, Mrp, Lrp) in the tumor tissue of the patient in dependence on the start of the cytokine treatment, the determination of the time period during which the expression of one or several MDR-associated genes is considerably reduced by the cytokine treatment, the treatment of the patient during the determined time period ("therapeutic window") with a therapeutically effective amount of a cytotoxic, MDR-associated substance, which is influenced (improved) in its efficacy by the expression of one or several MDR-associated genes.

Another object of the invention is a process for tumor therapy of patients with a MDR-associated cytotoxic substance, chemosensitization of tumor cells of a patient by cytokines, the determination of the level of one or more MDR-associated genes (e.g. mdr1, Mrp, Lrp) in the tumor tissue of the patient in dependence on the start of the cytokine treament, determination of the time period during which the expression of one or several MDR-associated genes is considerably reduced by the cytokine treatment, the treatment of the patient at the determined time period ("therapeutic window") with a therapeutically effective amount of a cytotoxic, MDR-associated substance, which is influenced (improved) in its efficacy by the expression of one or several MDR-associated genes.

Thus, as used throughout the disclosure and the claims, "therapeutic window" means the patient-specific time period during which the expression of one or more MDR-associated genes is substantially reduced by the treatment with cytokine.

It was surprisingly found that after treatment of a cancer patient, a patient-characteristic time course of expression of one or several MDR-associated genes can be observed in his tumor cells. It appears that, after cytokine treatment a "therapeutic window" can be determined, which is patient-specific and which can be exploited to advantage for the subsequent cytostatic treatment. This is particularly of importance if the tumor tissue of the patient is removed and a cytostatic treatment will be performed for prevention of progression. It has been surprisingly shown, that also in these cases one can refer to that "therapeutic window" for the subsequent treatment with one or several MDR-associated cytotoxic substances, which has been determined before removal of the tumor.

It has been shown, that particularly gastrointestinal tumors, melanomas,, sarcomas, mammary carcinomas and glioblastomas can be treated with the procedure of the invention.

Under "cytotoxic substance" a substance is meant which is used as medicament for the treatment of malignant diseases and which acts on the basis of cytotoxicity mainly towards tumor cells. Such cytotoxic substances, which belong to the spectrum of multidrug resistance include for example daunorubicin, doxorubicin, mitoxantrone, etoposid, tenoposid, vinblastine, vincristine, actinomycin D, mitomycin C, taxol (paclitaxel), topotecan, colchicine, emetin, ethidiumbromide, puromycin, gramicidin D, valinomycin and mithramycin. Such substances and their mode of action are described e.g. by U. A. German et al. in European Journal of Cancer 32A (1996):927–944. Cisplatinum can likewise be suitable cytotoxic substances.

Under "cytokine" a substance is meant, which posses as cellular, physiological messenger immunstimulatory or also cytostatic properties and which can be used for cytotoxic or cytostatic tumor therapy. Suitable cytokines include for example interleukins such as IL-2, interferons, such as IFNα and IFNy and tumor necrosis factors such as TNFα etc.

Under "multidrug resistance-associated gene" (MDR-associated gene) a gene is meant, which codes for a protein causally involved in the development of the multidrug resistance phenotype, such as e.g. the energy-dependent transmembrane drug efflux pump (mdr1, U. A. German et al. Eur. J. Cancer 32A (1996):927–944; Mrp, D. W. Loe et al. Eur. J. Cancer 32A (1996):945–957) or which causes the nucleo-cytoplasmatic transport of a drug (e.g. Lrp, Izquierdo et al. Eur. J. Cancer 32A (1996): 979–984).

The expression of MDR-associated genes can be determined at both levels (mRNA and protein) with known molecular-biological techniques, e.g. with RT-PCR and/or Northern-hybridization using isolated RNA or mRNA, respectively, and/or with in situ RT-PCR in cryosections of the tumor samples. At the protein level the determination of MDR-associated gene products can be performed with e.g. Western-blotting using isolated proteins and/or with the method of immunohistochemistry in cryosections using the respective specific antibodies.

The time interval at which the expression of MDR-associated genes is considerably reduced can be determined by the time-dependent in vitro analysis of tumor samples, e.g. from biopsies taken daily (before treatment and 24, 48, and 72 hours after cytokine application); the above mentioned methods are employed..

Under "considerably" or "substantially reduced" is meant that if at least a two-fold reduction in mRNA and/or protein of the respective MDR-associated gene is determined.

Determination of expression of the MDR-associated genes is performed in the tumor tissue of the patient. For this, biopsies are taken. The mRNA of MDR-associated genes can be determined by in situ RT-PCR and the respective gene products can be determined by immunohistochemistry in cryosections. Beside these statements on heterogeneity of tumor cell areas and on expression of these genes in tumor cell areas, the level of expression of the genes is determined by quantitative methods (e.g. RT-PCR with isolated RNA) using external and internal standards.

The cytokine treament can be performed by using one cytokine, suitably IL-2, IFNα, IFNy or TNFα or combinations of them, preferabely TNFα/IFNy or IFNα/IL2.

The treatment can be performed systemically or locally (e.g. perfusion of cytokines or cytokine-gene-therapy). It is preferred in the first step to treat the tumor tissue of the patient systemically or locally with one cytokine or combinations of them and in the last step to use the cytotoxic substance or their combinations locally or systemically. The cytokine is used at therapeutic concentrations, which will chemosensitize the tumor cells.

The cytokine is locally applied intratumorally, for which the cytokine itself or a nucleic acid, mediating the expression of the desired cytokine gene in the tumor cell, is utilized (e.g. local gene therapy, gene gun).

The cytotoxic substance is used at a therapeutically efficient concentration, which is destroying tumor cells in vivo to an appreciable extent.

The following example and the aforementioned publications explain the present invention. The process of the following examples is an exemplary illustration which can be modified.

EXAMPLE 1

Individual, patient-specific time courses of mdr1 gene expression after cytokine (IL-2) application in e.g. malignant melanomas

| | | mdr1-expression | | | |
|---|---|---|---|---|---|
| patient | analysis | prior to IL-2 treatment | 1. day post treatment | 2. day post treatment | 3. day post treatment |
| 1 | 1. | ++ | ++ | + | ++ |
| 1 | 2. | ++ | n.d. | n.d. | n.d. |
| 2 | 1. | +++ | + | ++++ | ++++ |
| 2 | 2. | +++ | + | ++ | ++++ |
| 2 | 3. | +++ | + | ++ | n.d. |
| 3 | 1. | ++ | ++++ | ++++ | ++++ |
| 4 | 1. | − | | | |
| 5 | 1. | ++++ | ++ | ++ | − |
| 5 | 2. | ++++ | ++ | + | n.d. |

− = negative, no mdr1 gene expression detectable
+ = mdr1 gene expression detectable, expression levels (+, ++, +++, ++++) are determined with respect to standards which were analyzed in parallel (genes with unaffected expression like β-actin and β-microglobulin, standard deviation 20%)
n.d. = no tumor material available The use of cytokine amounts in tumor therapy is very variable, depends on e.g. mode of application (i.v., s.c., bolus etc.) and is often individually fixed for the patient (M. H. Oppenheim et al. Oncology 51 (1994):154–169; S. Sone et al. Oncology 51 (1994):170–176; U. Hieber et al. Oncology 51 (1994):142–153; S. S. Agarwala et al. Oncology 51 (1994):129–136). Concentration ranges for the appropriate cytokines are:

| IL-2 | range | $3–20 \times 10^6$ IU/m$^2$/day | systemically |
| | | 1000–30.000 IU | locally |
| TNFα | range | 5–250 µg/m$^2$ | systemically |
| | | 100–250 µg/m$^2$ | locally |
| interferons | range | $2–50 \times 10^6$ IU/m$^2$/day | systemically |
| | | $6–10 \times 10^6$ IU | locally |

References

S. S. Agarwala et al., Oncology 51 (1994) 129–136
C. H. Evans et al., Cancer Res. 52 (1992) 5893–5899
A. T. Fojo et al., Proc. Natl. Acad. Sci. USA 84 (1987) 265–269
U. A. Germann et al., Semin. Cell. Biol. 4 (1993) 63–76
U. A. Germann Eur. J. Cancer 32A (1996) 927–944
U. Hieber et al., Oncology 51 (1994) 142–153
M. A. Izquierdo et al., Eur. J. Cancer 32A (1996) 979–984
J. Kellen Anticancer Res. 13 (1993) 959–961
D. W. Loe et al., Eur. J. Cancer 32A (1996) 945–957
M. Mousseau et al., Eur. J. Cancer 29A (1993) 753–759
K. Nooter et al., Br. J. Cancer 63 (1991) 663–669
M. H. Oppenheim et al., Oncology 51 (1994) 154–169

K. E. Sampson et al., Cancer Lett. 68 (1993) 7–14
S. Sone et al., Oncology 51 (1994) 170–176
U. Stein et al., Br. J. Cancer 74 (1996), in press
U. Stein et al., J. Natl. Cancer Inst. 88 (1996), in press
W. Walther et al., Cancer Res. Clin. Oncol. 120 (1994) 471–478
W. Walther et al., Int. J. Cancer 61 (1995) 832–839

What is claimed is:

1. A process for treating cancer with a cytotoxic agent comprising.
   (a) administering to the tumor cells of a patient a cytokine that downregulates the expression of one or more MDR-associated genes,
   (b) determining at various times after said administration of said cytokine in step (a) the level of expression of one or more MDR-associated genes in said tumor cells from biopsies taken from said patient,
   (c) determining the therapeutic window, said therapeutic window being the time after said administration of said cytokine in step (a) wherein expression of the one or more MDR-associated genes is downregulated; and
   (d) administering a therapeutically effective amount of said cytotoxic agent to said patient within said therapeutic window.

2. The process of claim 1, wherein said cytotoxic agent is selected from the group consisting of an anthracycline, an epiphyllotoxin, a vinca alkaloid and a cis-platinum compound, and one or more cytokines is selected from the group consisting of IL-2, GM-CSF, TBα, IFNα, and IFNy.

3. The process of claim 1, wherein said chemosensitizing step and said treating step takes place locally or systemically.

4. The process of claim 1, which comprises carrying out said steps (a) through (d) a plurality of times.

5. The process of claim 1, further comprising the partial or complete removal of the tumor of the patient.

* * * * *